United States Patent [19]

Napier et al.

[11] Patent Number: 5,284,776
[45] Date of Patent: Feb. 8, 1994

[54] AQUEOUS QUINOLONE CONCENTRATION ASSAY

[75] Inventors: James J. Napier, Lindenhurst; Mark R. Holst, Waukegan; Bhi-Yung Cheng, Northbrook, all of Ill.

[73] Assignee: Abbott Laboratories, Abbott Park, Ill.

[21] Appl. No.: 107,556

[22] Filed: Aug. 17, 1993

[51] Int. Cl.$^5$ .................. G01N 21/00; G01N 21/75
[52] U.S. Cl. .................... 436/764; 436/129; 436/111; 422/61
[58] Field of Search .............. 436/164, 129, 111; 422/61

[56] References Cited

U.S. PATENT DOCUMENTS 3,992,386 11/1976 Schacht et al. .................. 260/287
4,053,626 10/1977 Schacht et al. .................. 424/275
5,162,523 11/1992 Keith et al. .................... 540/227

*Primary Examiner*—James C. Housel
*Assistant Examiner*—N. Bhat
*Attorney, Agent, or Firm*—Andreas M. Danckers

[57] ABSTRACT

A method of determining the concentration of a quinolone in an aqueous solution comprising reacting the quinolone with an iron salt under conditions and for a time period sufficient to form a color change in the aqueous solution and comparing the resulting color change to an appropriate standard, and optionally comprising the further step of adjusting the pH of the aqueous quinolone solution to a value of less than about 7.0 prior to reacting the aqueous solution with an iron salt, as well as a test kit useful for carrying out such a method.

10 Claims, No Drawings

AQUEOUS QUINOLONE CONCENTRATION ASSAY

FIELD OF THE INVENTION

The present invention is directed to the determination of the concentration of a quinolone antibiotic in a colorimetric assay by reacting the quinolone with an iron salt.

BACKGROUND OF THE INVENTION

Quinolones are a class of compounds that are useful as broad spectrum antibiotics, especially for serious systemic infections. Quinolone antibiotics are used to treat infections in both humans and animals. For example, ciprofloxacin, a fluoroquinolone, is indicated for the treatment of urinary tract infections, lower respiratory infections, skin and skin suture infections, and bone and joint infections.

In many human and veterinary applications, quinolones may be administered in an aqueous solution. For example, colibacillosis in poultry can be treated by using a stock solution of sarafloxacin, subsequently diluted in the animals' drinking water via a "proportioner". Chickens require a dosage of 20 ppm of sarafloxacin in water, while turkeys require a dosage of 30 ppm. If the stock solution is not properly diluted by the proportioner, the animals may not receive the proper therapeutic dose of the quinolone antibiotic.

Quinolones in solution can be detected and their concentration determined by high performance liquid chromatography (HPLC). However, HPLC is difficult, time consuming, and requires skilled personnel to conduct the assays and interpret the results. HPLC is particularly burdensome when tests must be conducted outside of the analytical laboratory setting, such as on farms.

A more useful approach would be to have a method for determining the concentration of quinolones that is not as complicated and time consuming as HPLC, and that could be used outside of the analytical laboratory. In this way, adjustments in dosages can be accomplished quickly without having to wait overnight or days for results to be returned from the analytical laboratory, at which time the disease condition being treated may have worsened.

SUMMARY OF THE INVENTION

The present invention is directed to a method of determining the concentration of a quinolone in an aqueous solution comprising reacting the quinolone with an iron salt under conditions and for a time period sufficient to form a color change in the aqueous solution and comparing the resulting color to an appropriate standard. Preferably, the quinolone is difloxacin or sarafloxacin.

The iron salt is a ferric salt or a ferrous salt. A preferred ferric salt is ferric chloride.

In another embodiment, the present invention is directed to the above method further comprising the step of adjusting the pH of the aqueous quinolone solution to a value of less than about 7.0 prior to reacting the aqueous solution with the iron salt. Preferably, the pH value is adjusted by the addition of an acid. A preferred acid is hydrochloric acid.

In a further embodiment, the present invention is directed to a test kit for determining the concentration of a quinolone comprising a container containing an iron salt.

The iron salt of the test kit is preferably a ferric salt or a ferrous salt. The ferric salt is preferably ferric chloride.

In a still further embodiment, the test kit further comprises a container containing an acid. The acid is preferably hydrochloric acid.

In a yet further embodiment, the test kit further comprises a color standard.

In yet another embodiment, the test kit further comprises a container containing a quinolone standard. Preferably, that quinolone is sarafloxacin or difloxacin.

DETAILED DESCRIPTION OF THE INVENTION

The present invention is directed to a method of determining the concentration of a quinolone in an aqueous solution comprising reacting the quinolone with an iron salt under conditions and for a time period sufficient to form a color change in the aqueous solution and comparing the resulting color to an appropriate standard.

The prototypical quinolone is nalidixic acid, the structure of which is shown below:

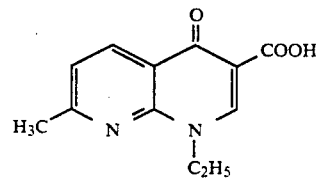

Numerous other quinolones are known, many of which are synthetic compounds. Quinolones of interest in veterinary medicine include sarafloxicin and difloxacin, which structures are shown below:

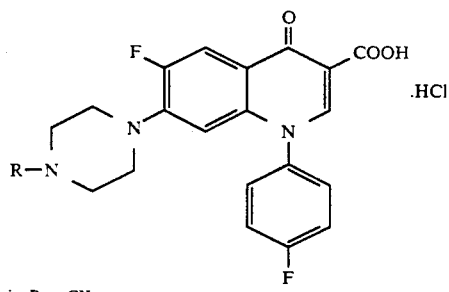

Difloxacin: R = CH$_3$
Sarafloxacin: R = H

Quinolones that can be used in the method of the present invention include ciprofloxacin, danofloxacin, enrofloxacin, ofloxacin, lomefloxacin, norfloxacin, difloxacin, sarafloxacin and nalidixic acid. More generally, quinolones containing 4 oxo and 3-carboxylic acid functional groups, or even more generally, quinolones containing a carboxylic acid group ortho relative to the oxo group, can be assayed with the method of the present invention.

The quinolone whose concentration is to be determined may be in the drinking water of animals when the quinolone is used in veterinary treatment. In this way, the dosage of the quinolone in the drinking water can be readily ascertained, so that the animals are assured of being given an appropriate therapeutic dose.

The quinolone in an aqueous solution is reacted with an iron salt typically by admixing the iron salt with the aqueous solution. The admixing is conducted under conditions and for a time period sufficient for the appropriate chemical interactions to occur in order for the aqueous solution to change color.

As is well known in the art, the conditions and time period for such reaction to occur depend on numerous factors, including temperature, time, pH, solubility of the iron salt, solubility of the quinolone, hardness of the water and other such factors. The average skilled worker in the art can readily determine the appropriate conditions and time period for the concentration of the quinolone to be determined by a color change.

While not wishing to be bound by theory, the quinolone to be assayed is thought to form an iron chelate reaction product as shown below:

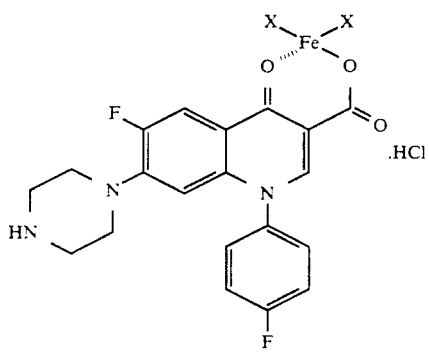

In the compound directly above, X refers to the counterion of the iron salt used. The quinolone iron chelate shown above is that of sarafloxacin reacted with a ferric salt. The ferric chloride chelate of sarafloxacin (when X=Cl in the compound above) gives a yellow color, which is concentration dependent. It is expected that such colored chelates will form with any quinolone used.

Iron, as is well known in the art of inorganic chemistry, exists in several ionic forms, but most often is found as iron(II), the ferrous ion, or iron(III), the ferric ion. The ferric ion is more likely to form coordination complexes, and so is preferred for the method of the present invention.

Exemplary iron salts that are useful in the present invention can be divided into ferric salts and ferrous salts. Both ionic forms of iron form dihalide compounds with all four of the common halogens, and form trihalide compounds with all of these common halides except iodine. Exemplary ferric salts include ferric ammonium citrate, ferric ammonium sulfate, ferric chloride, ferric citrate, ferric fluoride, ferric nitrate, ferric sulfate, and ferric tartrate. Exemplary ferrous salts include ferrous ammonium sulfate, ferrous chloride, ferrous fumarate, and ferrous sulfate. A ferric salt is preferred for the method of the present invention. An especially preferred ferric salt is ferric chloride.

In a further embodiment, the method of the present invention comprises the additional step of adjusting the pH of the aqueous quinolone solution to a value of less than about 7.0 prior to reacting that aqueous solution with iron. Preferably, the pH value of the solution is from about 1.0 to about 7.0, and more preferably from about 1.0 to about 3.0, and most preferably from about 1.0 to about 2.0.

Adjustment of the pH value to less than 7.0 is conducted, for example, to protonate chelating compounds such as EDTA, thereby preventing unwanted chelation of the iron used in the method of the present invention. If the particular aqueous solution of quinolone to be assayed does not contain compounds capable of chelating iron, or other inhibitory agents, then adjustment of the pH value is not considered necessary to practice the present invention.

The pH value of an aqueous solution can be adjusted by the judicious addition to that solution of either an acid or a base, as is well known in the art. If the aqueous solution has a pH value higher than the desired pH value, then the pH value is adjusted by the addition and admixing of an appropriate acid (e.g., hydrochloric acid). Conversely, if the aqueous solution has a pH value lower than the desired pH value, then the pH value is adjusted by the addition and admixing of an appropriate base (e.g., sodium hydroxide).

In a preferred embodiment, the adjustment of the pH value of the aqueous solution is accomplished by the addition of an acid. Preferably, that acid is hydrochloric acid.

The concentration of the quinolone is determined by a color change of the aqueous solution after the reaction between the quinolone and iron compound is complete, and a subsequent comparison of that resulting color change to an appropriate standard. Color formation is a result of the iron coordination complex thought to form as the reaction product, as discussed elsewhere herein. However, it is specifically contemplated that the reaction product indicating the concentration of a quinolone according to the method of the present invention can be detected by methods employing electromagnetic radiation outside of the visible range of colors, as discussed elsewhere herein, or by the use of other detection techniques, such as HPLC.

Color formation is best determined spectrophotometrically, such as by using an ultraviolet/visible light (UV/VIS) spectrophotometer for compounds that absorb light in the visible or ultraviolet light wavelength. The techniques of UV/VIS spectrophotometry are well known in the art, and will not be reiterated here except to state that the technique essentially requires the initial preparation of quinolone solutions of known concentration to yield a standard curve comparing color (as represented by absorbance or transmittance) against quinolone concentration. The color change of these standard solutions is compared against a "blank" standard, containing all of the components of the standard solution except the quinolone. In this way, any color initially present in the sample is accounted for, and the spectrophotometer measures only the change in color of the solution as a result of the presence of the quinolone reaction product.

A quinolone solution of unknown concentration is then assayed in the UV/VIS spectrophotometer, again compared against a blank standard, and the absorbance or transmittance value of the unknown quinolone sample is plotted on the linear portion of the standard curve, to compare the unknown quinolone sample to samples of quinolones of known concentration. By this comparison to an appropriate color standard, a precise quantitation of the concentration of the quinolone in the unknown sample can be determined.

The formation of an infrared-absorbing or fluorescent molecule can be detected by similar techniques, as is well known in the art.

Where spectrophotometry is not possible, such as in field testing for the detection of a quinolone, the resulting color of a test sample can be compared to the color of an appropriate "blank" standard, i.e., one which contains the same components as the test aqueous sample, minus a quinolone. This comparison can give a rough estimation of the mere presence or absence of the quinolone in the test sample.

The resulting color of the test sample may also be compared to a color chart of a quinolone standard, in order to determine the concentration of that quinolone. Such a color chart standard can be prepared by preparing known concentrations of a quinolone in an aqueous solution, and then subjecting these quinolone standards to the method of the present invention. Each known concentration will then produce a particular color, judged for example by using the American Public Health Administration (APHA) color, according to procedures well known in the art. This result would show that color formation is concentration-dependent, a necessary result for valid quantitation of an unknown quinolone sample.

This procedure, repeated so as to ensure statistical accuracy, forms the basis for a color chart standard of known quinolone concentrations. By comparing the resulting color of a test solution containing an unknown concentration of quinolone with the color chart standard, the concentration of the quinolone in that test solution can be determined within the precision of the color chart.

Thus, as used herein, the phrase "an appropriate standard" means, for example, a blank, as discussed above, or a color standard derived from aqueous solutions containing known concentrations of quinolones, as discussed above, either in the form of actual tubes of standard quinolones or a color chart, as discussed elsewhere herein. The standard must be appropriate for the quinolone used, as well as for the purpose for which the standard itself is used, that is, whether it is used for merely qualitative purposes, or whether it is used for more precise quantitation of the quinolone by determination of its concentration.

In another embodiment, the present invention is directed to a test kit for determining the concentration of a quinolone comprising a container containing an iron salt. The test kit provides the necessary reagent to conduct a field test for the determination of the concentration of a quinolone in an aqueous solution according to the method of the present invention.

A container may be, for example, a vial, test tube, box, or other container which holds either a liquid or solid material.

Preferably, the iron salt in the test kit is a ferric salt or a ferrous salt, as discussed elsewhere herein. The ferric salt is preferably ferric chloride. The iron salt in the test kit may be in solid form, with instructions for reconstitution with water into an appropriate stock solution, or may be present as a stock solution of appropriate concentration to practice the method of the present invention.

Thus, for example, the test kit may contain a 1% ferric chloride solution, or may contain 1 mg of solid ferric chloride, with instructions to dissolve the entire amount of ferric chloride in 100 ml of water to produce a 1% ferric chloride solution.

In a further embodiment, the test kit further comprises a container containing an acid. As discussed elsewhere herein, the method of the present invention optionally includes the adjustment of the pH value of the aqueous quinolone solution. The test kit optionally comprises an acid to accomplish this function. The acid is preferably hydrochloric acid.

In a still further embodiment, the test kit further comprises a color standard. As discussed elsewhere herein, the concentration of a quinolone in a test sample can be determined by comparing the resulting color of the sample following the reaction according to the method of the present invention to an appropriate standard. One such standard is a color standard comprised of, for example, sealed tubes of aqueous quinolone solutions of known concentration reacted with a ferric salt according to the method of the present invention. Another such standard is a color standard comprised of, for example, a color chart indicating the correlation between a particular color and the concentration of a quinolone solution of that color, against which the resulting color of the test solution of a quinolone can be compared.

In yet another embodiment, the test kit further comprises a container containing a quinolone standard. The quinolone in the test kit may be in solid form, with instructions for reconstitution with water into an appropriate stock solution, or may be present as a stock solution of a particular concentration.

Thus, for example, the test kit may contain a 40 ppm quinolone solution, or may contain an amount of solid quinolone with instructions to dissolve the entire amount of quinolone in 100 ml of water to produce a 40 ppm quinolone solution.

The quinolone is provided in the test kit to insure that the assay reagents are working properly. By providing a quinolone in the test kit, the user of the test kit can determine that the reagents in the test kit are fresh and function according to the method of the present invention to determine the concentration of a quinolone. By providing a quinolone of known concentration in the test kit, either as an aqueous solution or as a solid for reconstitution, the reacted quinolone can also serve as an appropriate standard, as discussed elsewhere herein.

The test kit may further comprise a blank as an appropriate standard, as discussed elsewhere herein.

Preferably, the quinolone is difloxacin or sarafloxacin, although the quinolones that can be used in the method of the present invention, discussed elsewhere herein, can also be used in the test kit.

The following examples further illustrate the invention and are not to be construed as limiting of the specification and claims in any way.

EXAMPLE 1

Basic Assay for Sarafloxacin in Chicken/Turkey Drinking Water

The assay requires the following reagents: 6N hydrochloric acid, reagent grade ferric chloride, and sarafloxacin WSP (water soluble product) of known concentration.

One gram of ferric chloride is dissolved in 100 ml of deionized $H_2O$ (with sonication, if necessary), to prepare a stock 1% ferric chloride solution.

The preparation of the sarafloxacin stock solution is begun by accurately determining the mass of the sarafloxacin component in a mass of sarafloxacin WSP. The mass of the sarafloxacin WSP is multiplied by the percent sarafloxacin in the sarafloxacin WSP to give the mass of the free sarafloxacin therein. A 20 mg/ml sarafloxacin solution is then prepared based upon this calculation.

The stock sarafloxacin solution is then diluted with distilled water into a 200 ml volumetric flask according to the following table:

TABLE 1

| Final Concentration | Amount of Stock |
| --- | --- |
| 0 ppm | 0 ml |
| 10 ppm | 1 ml |
| 20 ppm | 2 ml |
| 30 ppm | 3 ml |
| 40 ppm | 4 ml |

Next, 5 ml of each of the known concentration sarafloxacin standards is pipetted into a scintillation vial. One drop of the 6N HCl solution is added, and is mixed thoroughly. Then, 3 drops of the 1% ferric chloride stock solution is added, and is again mixed thoroughly. Color development is allowed to progress to completion for 30 seconds. These color standards are to be prepared fresh each day.

A test sample can be similarly assayed. Five ml of each sample is pipetted into a scintillation vial. One drop of 6N HCl is added and mixed thoroughly. Next, 3 drops of 1% ferric chloride is added, and is again mixed thoroughly. After 30 seconds, the color development is complete. The resulting color of the test sample is then compared to the color of the color standards, to determine the concentration in parts per million of the test sample.

EXAMPLE 2

Sarafloxacin Colorimetric Results

A five-member panel was assembled to analyze the results of the method of the present invention. Four different test samples of known sarafloxacin concentration, in parts per million, were prepared in the laboratory, according to the protocol of Example 1. These test samples were then given to each of the panel members, who were not told the concentrations, but were asked to assay each sample as if it were an unknown, again according to the protocol of Example 1. Each sample was therefore tested five times. The calculated mean concentration value of each sample, in parts per million, along with the actual concentration, is presented in the table below:

TABLE 2

| Sample ID | Actual Conc. (ppm) | Mean Conc. (ppm) |
| --- | --- | --- |
| B | 25.1 | 24.0 |
| C | 35.9 | 33.4 |
| D | 34.3 | 32.5 |
| E | 16.0 | 16.0 |

The data show that the accuracy of the method of the present invention ranges from 100% in the case of sample E to about 93% in the case of sample C.

The foregoing specification, including the specific embodiments and examples, is intended to be illustrative of the present invention and is not to be taken as limiting. Numerous other variations and modifications can be effected without departing from the true spirit and scope of the present invention.

We claim:

1. A method of determining the concentration of a quinolone in an aqueous solution comprising:
   (i) reacting said quinolone with an iron salt under conditions and for a time period sufficient to form a color change in said aqueous solution, and
   (ii) comparing said resulting color change to a colored standard derived from aqueous solutions containing known concentrations of quinolones, thereby determining the concentration of quinolone in said aqueous solution.

2. The method of claim 1 wherein said quinolone is difloxacin or sarafloxacin.

3. The method of claim 2 wherein said iron salt is a ferric salt or a ferrous salt.

4. The method of claim 3 wherein said ferric salt is ferric chloride.

5. The method of claim 1 further comprising the step of adjusting the pH of said aqueous solution to a value of less than about 7.0 prior to reacting said aqueous solution with said iron salt.

6. The method of claim 5 wherein said adjusting is by the addition of an acid.

7. The method of claim 6 wherein said acid is hydrochloric acid.

8. A test kit for determining the concentration of quinolone in an aqueous solution, consisting essentially of a container containing ferric chloride, a container containing hydrochloric acid, and a color standard derived from aqueous solutions containing known concentrations of quinolones.

9. The test kit of claim 16 further comprising a container containing a quinolone standard.

10. The test kit of claim 14 wherein said quinolone is sarafloxacin or difloxacin.

* * * * *